(12) United States Patent
Takezaki et al.

(10) Patent No.: US 11,904,356 B2
(45) Date of Patent: Feb. 20, 2024

(54) ULTRASONIC TRANSDUCER, MANUFACTURING METHOD THEREOF, AND ULTRASONIC IMAGING DEVICE

(71) Applicant: Hitachi, Ltd., Tokyo (JP)

(72) Inventors: Taiichi Takezaki, Tokyo (JP); Masakazu Kawano, Tokyo (JP); Shuntaro Machida, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 1118 days.

(21) Appl. No.: 16/699,185

(22) Filed: Nov. 29, 2019

(65) Prior Publication Data

US 2020/0171538 A1  Jun. 4, 2020

(30) Foreign Application Priority Data

Dec. 3, 2018  (JP) .................. 2018-226644

(51) Int. Cl.
| | |
|---|---|
| *B06B 1/02* | (2006.01) |
| *B81B 3/00* | (2006.01) |
| *B81C 1/00* | (2006.01) |
| *A61B 8/12* | (2006.01) |
| *A61B 8/00* | (2006.01) |
| *A61B 5/00* | (2006.01) |
| *G01N 29/24* | (2006.01) |

(52) U.S. Cl.
CPC .......... *B06B 1/0292* (2013.01); *A61B 5/0095* (2013.01); *A61B 8/12* (2013.01); *A61B 8/4494* (2013.01); *B81B 3/0021* (2013.01); *B81C 1/00158* (2013.01); *G01N 29/2406* (2013.01); *B81B 2201/0271* (2013.01); *B81B 2203/0127* (2013.01); *B81B 2203/0315* (2013.01); *B81B 2203/04* (2013.01); *B81C 2201/0105* (2013.01); *G01N 2291/101* (2013.01)

(58) Field of Classification Search
None
See application file for complete search history.

(56) References Cited

U.S. PATENT DOCUMENTS

| | | |
|---|---|---|
| 6,271,620 B1 | 8/2001 | Ladabaum |
| 6,571,445 B2 | 6/2003 | Ladabaum |
| 2007/0052093 A1 | 3/2007 | Machida et al. |

FOREIGN PATENT DOCUMENTS

| | | |
|---|---|---|
| JP | 2003-500955 A | 1/2003 |
| JP | 2009-165931 A | 7/2009 |
| JP | 4724501 B2 | 7/2011 |
| WO | 2015/159427 A1 | 10/2015 |

OTHER PUBLICATIONS

Notice of Reasons for Refusal dated Mar. 1, 2022, issued in corresponding Japanese Patent Application No. 2018-226644.

*Primary Examiner* — Alexander G Ghyka
(74) *Attorney, Agent, or Firm* — Mattingly & Malur, PC

(57) ABSTRACT

A highly-sensitive ultrasonic transducer with good yield is provided. The ultrasonic transducer includes a cavity layer, a pair of electrodes positioned above and below the cavity layer, insulating layers disposed above and below each of the pair of electrodes, and a filled hole that penetrates, in a vertical direction, at least a portion of the insulating layers positioned above the cavity layer. When the ultrasonic transducer is viewed from above, each electrode of the pair of electrodes includes, at a position that overlaps the embedded hole, a non-electrode region where the electrodes are not formed.

4 Claims, 8 Drawing Sheets

A-A CROSS-SECTIONAL VIEW

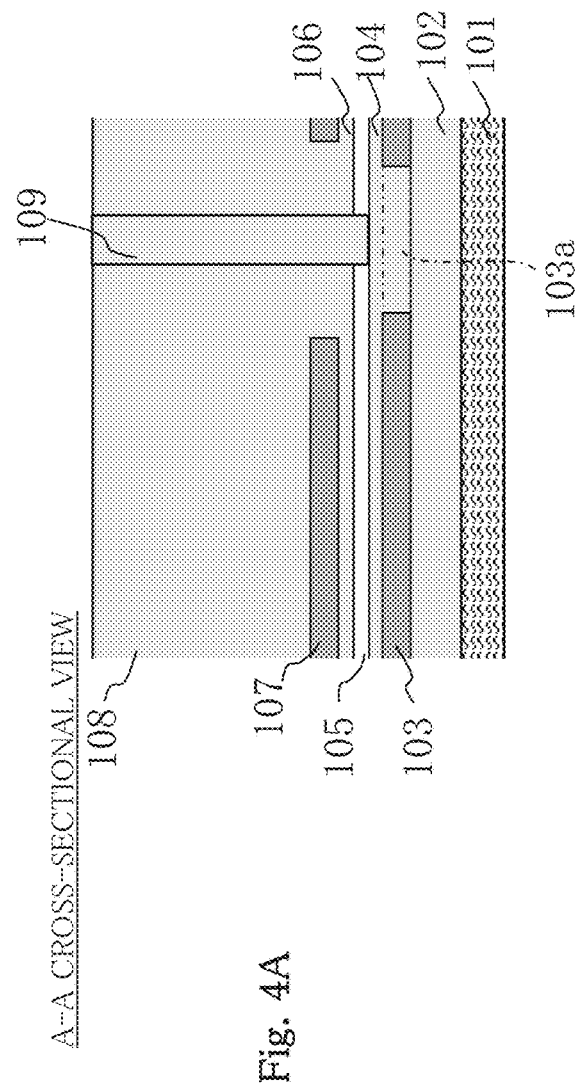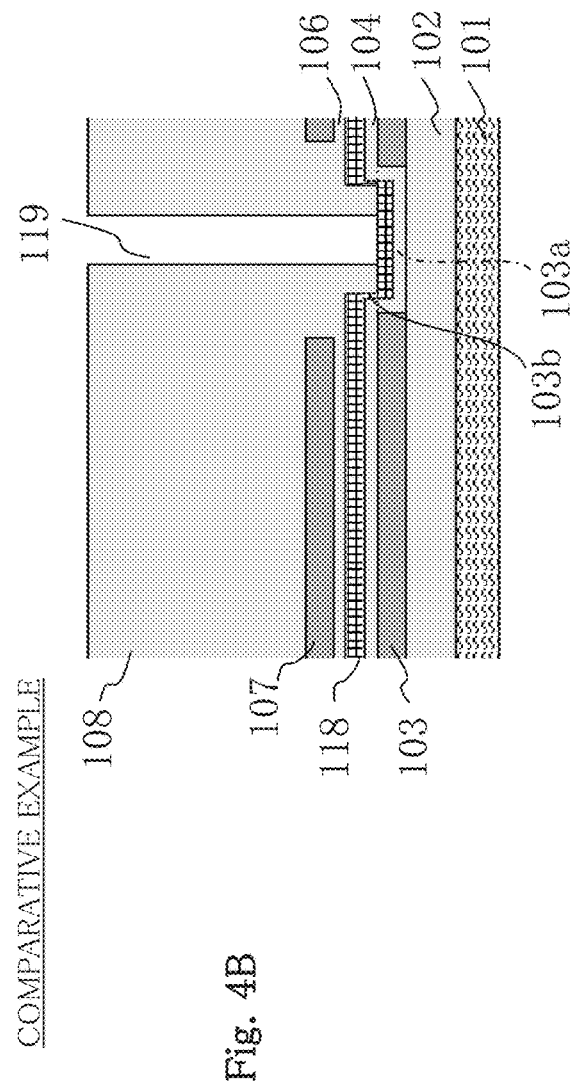

B-B CROSS-SECTIONAL VIEW

ULTRASONIC TRANSDUCER, MANUFACTURING METHOD THEREOF, AND ULTRASONIC IMAGING DEVICE

INCORPORATION BY REFERENCE

The present application claims priority from Japanese patent application JP-2018-226644 filed on Dec. 3, 2018, the content of which is hereby incorporated by reference into this application.

BACKGROUND OF THE INVENTION

Field of the Invention

The present invention relates to a manufacturing technique for an ultrasonic transducer, and particularly relates to a technique that is effective for application to the structure of an ultrasonic transducer manufactured by micro electro mechanical system (MEMS) technology.

Description of the Related Art

Ultrasonic transducers are used in a variety of applications including ultrasonic imaging devices which, inspect human bodies, the internal structure of objects, and the like by transmitting and receiving ultrasonic waves.

Conventionally, ultrasonic transducers that utilize the vibration of piezoelectric materials have been used, but MEMS technology has advanced in recent years and capacitive micromachined ultrasonic transducers (CMUT) have been developed. In CMUTs, a vibration unit is fabricated on a silicon substrate.

A CMUT is a vibration device that has a structure in which upper and lower electrodes are disposed so as to sandwich a cavity layer, and the cavity layer is covered with insulating layers. CMUTs utilize the phenomenon whereby electrostatic force is generated in a membrane on top of the cavity as a result of voltage being applied between the upper electrode and the lower electrode to generate a potential difference. Ultrasonic waves are transmitted by varying the voltage applied to the upper and lower electrodes over time to cause the membrane to vibrate. The ultrasonic waves are received by detecting, as voltage change or current change, displacement of the membrane while applying constant voltage between the upper and lower electrodes.

In a method for forming the cavity layer between the upper and lower electrodes, first, a metal membrane (sacrifice layer) is disposed between vertically laminated electrodes. Insulating layers are deposited around the electrodes and the sacrifice layer. Then, a through-hole that penetrates the insulating layer is formed and an etchant is introduced via the through-hole. As a result, the sacrifice layer is etched and removed, and the cavity layer is formed.

For example, the CMUT disclosed in Japanese Patent No. 4724501 includes a cavity layer formed between an upper electrode and a lower electrode, a through-hole for forming the cavity layer by etching, and first insulating layer that includes a projection that extends into the cavity layer from above, wherein the through-hole is filled with an insulating material. The projection provided in this CMUT fulfills the role of a support structure, thereby preventing the entire lower surface of the first insulating layer from contacting the insulating layer covering the lower electrode when voltage is applied, and reducing the amount of charge injected into the insulating layers.

Japanese Patent Application Publication No. 2009-165931 discloses a CMUT that uses a silicon single-crystal membrane with good mechanical properties as the membrane. In this CMUT, the through-hole and the lower electrode are disposed at positions that do not overlap when viewed from above.

SUMMARY OF THE INVENTION

It is known that the sensitivity of the ultrasonic transducers of the CMUTs such as the CMUTs disclosed in above patent documents increases as the distance between the upper and lower electrodes decreases. However, when the distance between the upper and lower electrodes is reduced, the through-hole for etchant introduction may reach the upper electrode or the lower electrode at the time of manufacturing. If the etchant is introduced via the through-hole in a state in which the through-hole reaches an electrode, the etchant may reach and dissolve the electrode.

An object of the present invention is to provide a highly-sensitive ultrasonic transducer with good yield.

To achieve the object described above, the ultrasonic transducer according to the present invention includes a cavity layer, a pair of electrodes positioned above and below the cavity layer, insulating layers disposed above and below each of the pair of electrodes, and a filled hole that penetrates, in a vertical direction, at least a portion of the insulating layer positioned above the cavity layer. In addition, when this ultrasonic transducer is viewed from above, each electrode of the pair of electrodes includes, at a position that overlaps the filled hole, a non-electrode region where the electrode is not formed.

In addition, a manufacturing method for the ultrasonic transducer according to the present invention includes sequentially laminating, on a substrate, a first electrode, a first insulating layer, a sacrifice layer, a second insulating layer, a second electrode, and a third insulating layer; forming a through-hole that penetrates from the third insulating layer to the sacrifice layer; forming a cavity layer by etching and removing, via the through-hole, a material of the sacrifice layer; and filling the through-hole with an insulating material. In this manufacturing method, when respectively laminating the first electrode and the second electrode, a region that includes a region corresponding to the through-hole when the ultrasonic transducer is viewed from above, is defined as a non-electrode region, and the first electrode and the second electrode are each deposited in regions other than the non-electrode region.

According to the present invention, the distance between the upper and lower electrodes can be reduced compared to conventional technology. With the ultrasonic transducer of the present invention, the lower electrode is disposed only below the cavity layer that vibrates when driving and is not disposed below the filled hole. As such, the capacitance component that does not contribute to lower electrode vibration, that is, parasitic capacitance, can be reduced. As a result, the sensitivity of the ultrasonic transducer can be increased.

Additionally, with the manufacturing method for the ultrasonic transducer according to the present invention, it is possible to provide a highly reliable ultrasonic transducer with good yield.

BRIEF DESCRIPTION OF THE DRAWINGS

FIG. 4A is a cross-sectional view of the ultrasonic transducer according to Embodiment 2, taken along line A-A of FIG. 1;

FIG. 4B is a cross-sectional view of an ultrasonic transducer according to a comparative example;

FIGS. 5A to 5C are cross-sectional views illustrating a filling and flattening method for a non-electrode region 103a and an upper region of the non-electrode region 103a;

DETAILED DESCRIPTION OF THE INVENTION

Next, embodiments of the present invention will be described using the drawings.

Figure 1:
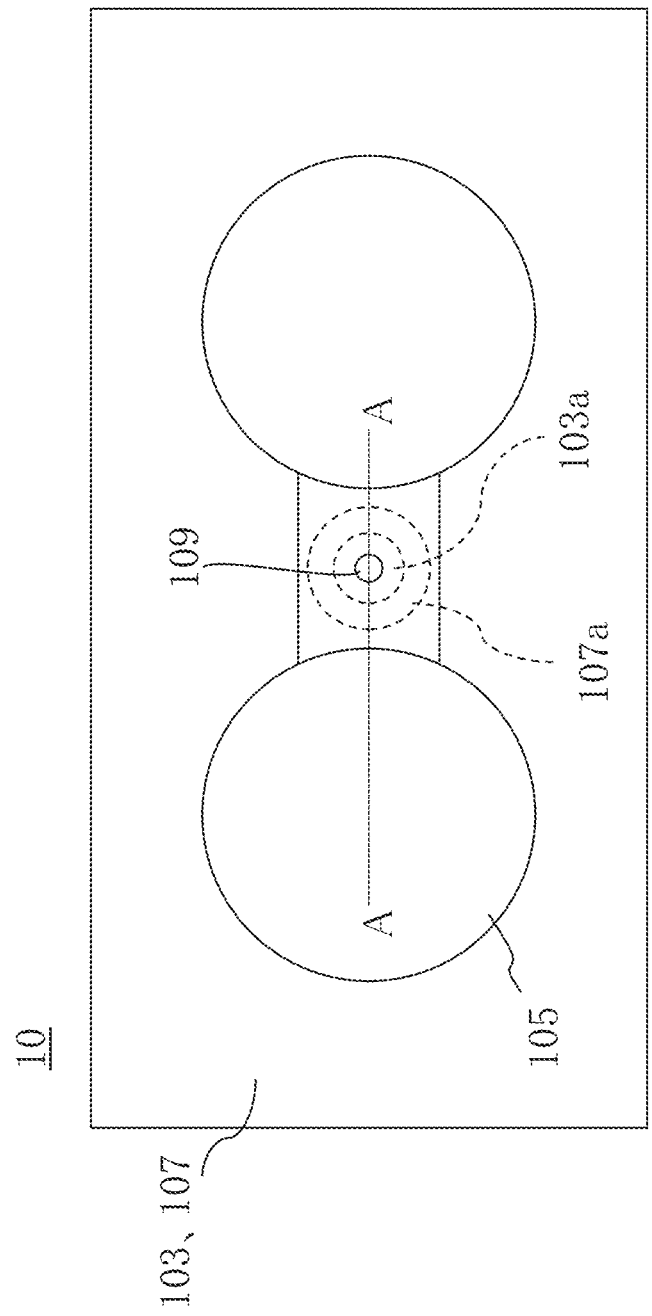
FIG. 1 is a top view of an ultrasonic transducer 10 that is common to Embodiments 1 and 2 according to the present invention.
Figure 2:
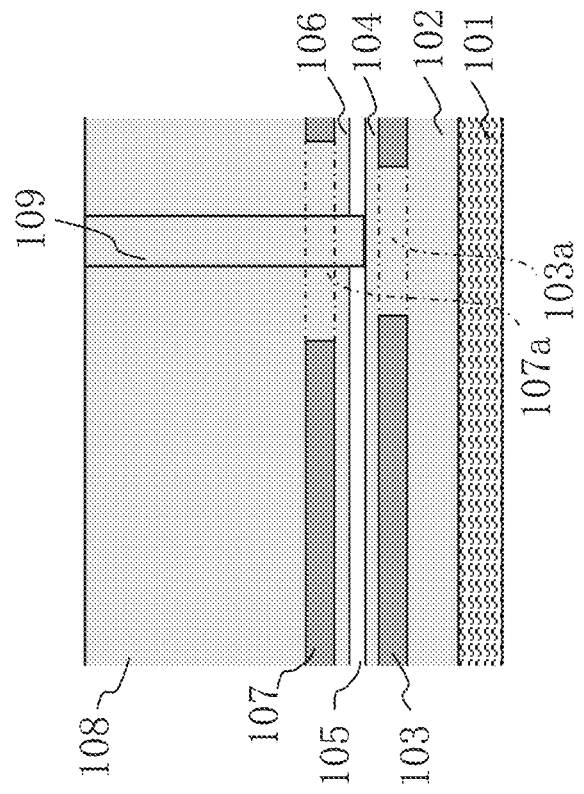
FIG. 2 is a cross-sectional view of the ultrasonic transducer according to Embodiment 1, taken along line A-A of FIG. 1.

First, an overview of the configuration of an ultrasonic transducer 10 according to the present invention will be described while referencing FIGS. 1 and 2. The ultrasonic transducer 10 is a so-called CMUT, which is formed by MEMS technology on a substrate 101. The ultrasonic transducer 10 may be a single element or may be a CMUT array or CMUT chip in which a plurality of CMUT elements are arranged. Hereinafter, a case in which a plurality of CMUT elements are disposed in the ultrasonic transducer 10 is described. FIG. 1 illustrates two elements of the plurality of CMUT elements of the ultrasonic transducer 10 according to the present invention. FIG. 2 illustrates a cross-sectional view of FIG. 1, taken along line A-A. In FIG. 1, the CMUT elements are depicted as circles for the sake of description but, in this example, the shape of the elements is not limited thereto.

The ultrasonic transducer 10 includes a cavity layer 105, a pair of electrodes (upper electrode 107 and lower electrode 103) positioned above and below the cavity layer 105, insulating layers 102, 104, 106, and 108 disposed above and below each of the pair of electrodes 107 and 103, and a filled hole 109 that penetrates, in a vertical direction, at least a portion of the insulating layers 106 and 108 positioned above the cavity layer 105. As illustrated in FIG. 1, the upper electrode 107 includes a non-electrode region 107a, where an electrode is not formed, and the lower electrode 103 includes a non-electrode region 103a where an electrode is not formed. The non-electrode regions 107a and 103a are formed at positions that overlap the filled hole 109 when the ultrasonic transducer 10 is viewed from above.

The filled hole 109 is obtained by filling a through-hole used for forming the cavity layer 105 with an insulator, and is formed among the various CMUT elements. That is, the filled hole 109 is disposed in a region other than above the cavity layer 105. Due to this configuration, the filled hole 109 does not vibrate when driving.

With the ultrasonic transducer 10 described above, the lower electrode 103 is disposed only below the cavity layer 105 that vibrates when driving and is not disposed below the filled hole 109. As such, the capacitance component that does not contribute to the vibration of the lower electrode 103, that is, the parasitic capacitance, can be reduced and the sensitivity of the ultrasonic transducer 10 can be increased.

In addition, when the ultrasonic transducer 10 is viewed from above, the filled hole 109 is disposed at a position that does not overlap with the pair of upper and lower electrodes 107 and 103. As such, even if the distance between the upper and lower electrodes is reduced compared to conventional technology (on the order of tens of nm), the through-hole can be prevented from reaching the upper electrode 107 and the lower electrode layer 103 when forming the through-hole prior to filling the filled hole 109, regardless of the depth accuracy of the through-hole. As a result, it is possible to provide a highly-sensitive ultrasonic transducer.

Embodiment 1

Hereinafter, the configuration of an ultrasonic transducer according to Embodiment 1 will be described in detail while referencing FIGS. 1 and 2.

The components described above are disposed on a substrate 101 that is formed from a single-crystal silicon or similar semiconductor substrate. Specifically, the insulating layer 102, a first electrode (lower electrode) 103, a first insulating layer 104, the cavity layer 105, a second insulating layer 106, a second electrode (upper electrode) 107, and a third insulating layer 108 are laminated sequentially on a top surface of the substrate 101. The non-electrode regions 107a and 103a are filled with an insulating material, and the non-electrode regions 107a and 103a are formed from insulators.

The filled hole 109 penetrates the non-electrode region 107a of the upper electrode 107 in the vertical direction. In Embodiment 1, when viewed from above, the non-electrode region 103a of the lower electrode 103 is smaller than the non-electrode region 107a of the upper electrode 107. However, it is sufficient that, when viewed from above, the non-electrode region 103a and the non-electrode region 107a are larger than the filled hole 109, and the sizes of the non-electrode region 103a and the non-electrode region 107a are not limited to the example described above. In addition, provided that the non-electrode regions 103a and 107a have shapes that surround the filled hole 109, the shapes, when viewed from above, of the non-electrode regions 103a and 107a are not limited to round shapes such as those illustrated in FIG. 1.

The non-electrode regions 107a and 103a are filled with an insulating material, and the non-electrode regions 107a and 103a are formed from insulators. The insulating layers 102, 104, 106, and 108 (described later) may be formed from the same material or may be formed from different materials.

Aside from single-crystal silicon, glass, quartz, sapphire, and the like can be used as the material of the substrate 101.

Aluminum (Al) with a thickness of about 10 nm to 1000 nm may be used as the upper electrode 107 and the lower electrode 103. Examples of materials other than Al that may be used include metal materials such as Al alloys, W, Ti, TiN, Ni, Co, Cr, Pt, and Au, polycrystalline silicon or amorphous silicon doped with impurities at high concentrations, and indium tin oxide (ITO). The upper electrode 107 and the lower electrode 103 may be formed from the materials described above as single layer or as laminated membranes.

The insulating layers 102, 104, 106, and 108 may be formed from the same material or may be formed from different materials. These insulating layers may be configured as single layer or as a laminated membrane formed from one or two or more selected from silicon oxide ($SiO_2$), silicon nitride ($Si_3N_4$), aluminum oxide ($Al_2O_3$), titanium oxide ($TiO_2$), zirconium oxide ($ZrO_2$), hafnium oxide ($HfO_2$), silicon-doped hafnium oxide, and the like. The various insulating layers may be the same material or may be different materials. The filled hole 109 may be filled with the same material as the above-described insulating material.

For the insulating layer 102, a material with good adhesiveness to the substrate material and the material of the lower electrode 103, which is formed on the insulating layer 102, is selected. Since the insulating layer 104 is a portion in which high electrical fields are generated, a material with high voltage resistance such as $SiO_2$ is preferable. The material of the insulating layer 106 preferably has high voltage resistance, similar to the insulating layer 104. The insulating layers 106 and 108 form a membrane together with the upper electrode 107 and are displaced when transmitting and receiving ultrasonic waves. As such, it is preferable that the membrane shape is flat prior to displacement and, for the insulating layers 106 and 108, a plurality of layers are laminated using a material with tensile stress such as SiN and a material with compressive stress such as $SiO_2$, thereby ensuring flatness.

A thickness of the insulating layer 102 may be set to about 10 nm to 10,000 nm, a thickness of the insulating layer 104 may be set to 1 nm to about 1,000 nm, a thickness of the insulating layer 106 may be set to about 1 nm to 1,000 nm, and a thickness of the insulating layer 108 may be set to about 10 nm to 10,000 nm.

The cavity layer 105 is formed on a top surface of the insulating layer 104 and with a thickness of about 1 nm to 1,000 nm such that the top and bottom of the cavity layer 105 are flat surfaces. The interior of the cavity layer 105 is hollow.

Manufacturing Method for the Ultrasonic Transducer according to Embodiment 1

Next, a manufacturing method for the ultrasonic transducer according to Embodiment 1 will be described while referencing FIGS. 3A to 3F.

Figure 3A:
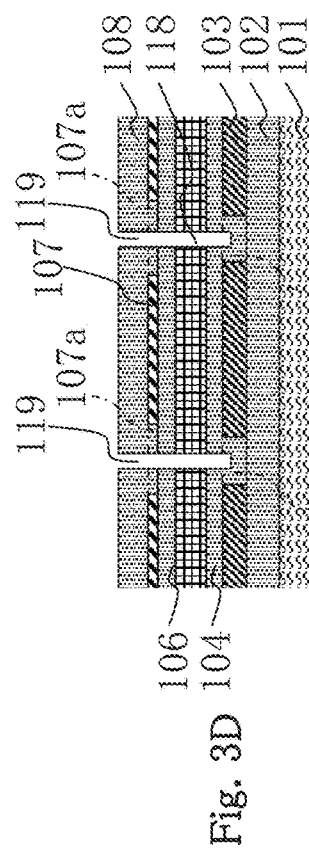
FIGS. 3A to 3F are cross-sectional views illustrating a manufacturing method for the ultrasonic transducer according to Embodiment 1.

First, as illustrated in FIG. 3A, the insulating layer 102 and the lower electrode 103 are sequentially formed on the substrate 101. The insulating layer 102 may be formed by a known film depositing technique such as plasma CVD or vapor deposition. The lower electrode 103 is deposited on an entire top surface of the insulating layer 102 by the same method used for depositing the insulating layer 102. Then, the lower electrode 103 is patterned using a photolithographic method, a dry etching method, or the like. When the ultrasonic transducer is viewed from above, the lower electrode 103 is not formed in the non-electrode region 103a, which is the region (below the region where the through-hole 119 is to be formed) that includes the region corresponding to the through-hole 119.

Figure 3B:
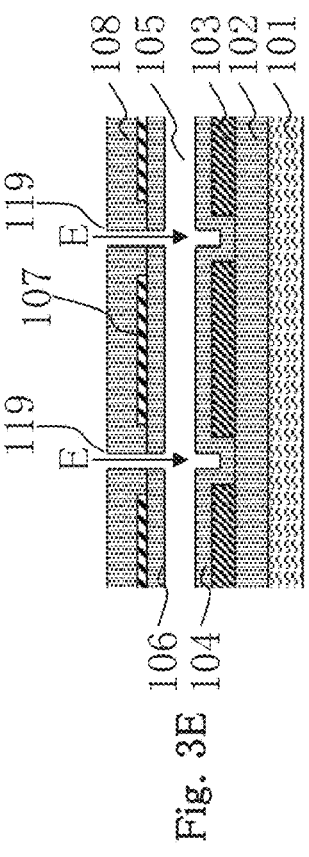

Next, as illustrated in FIG. 3B, the insulating material is coated on a top surface of the lower electrode 103, the non-electrode region 103a, and an upper region of the non-electrode region 103a. As a result, an insulating layer 104 with a flat top surface is formed. A known film depositing technique such as plasma CVD or vapor deposition may be used as the method for depositing the insulating layer 104.

A metal membrane (sacrifice layer) 118 is formed on a top surface of the insulating layer 104 by sputtering or the like. The sacrifice layer 118 is a layer that is temporarily provided to form the cavity layer 105, and is later etched and removed by an etchant. Polycrystalline silicon is used as the material of the sacrifice layer 118. The thickness of the sacrifice layer determines the height of the cavity layer 105 and, as such, the sacrifice layer is formed with excellent thickness uniformity, and has a thickness of about 1 nm to 1,000 nm.

Figure 3C:
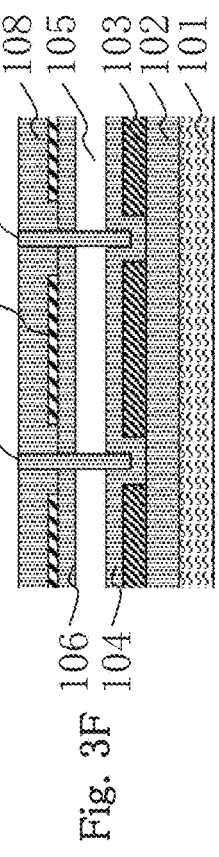

Next, as illustrated in FIG. 3C, the insulating layer 106 is deposited on a top surface of the sacrifice layer 118 by a known film depositing technique such as plasma CVD or vapor deposition.

The upper electrode 107 is formed on a top surface of the insulating layer 106. The upper electrode 107 is formed on the entire top surface of the insulating layer 106 and, then, is patterned using a photolithography method, a dry etching method, or the like. When the ultrasonic transducer 10 is viewed from above, the upper electrode 107 is deposited in a region other than the non-electrode region 107a, which includes the region corresponding to the through-hole 119 (through which the through-hole is to be opened). At this time, it is preferable that the upper electrode 107 is patterned such that the non-electrode region 107a of the upper electrode 107 is wider than the non-electrode region 103a of the lower electrode 103.

After the upper electrode 107 is formed, the insulating material is coated on the top surface of the upper electrode 107, the non-electrode region 107a, and the upper region of the non-electrode region 107a. As a result, an insulating layer 108 with a flat top surface is formed. A known film depositing technique such as plasma CVD or vapor deposition may be used as the method for forming the insulating layer 108.

Figure 3D:
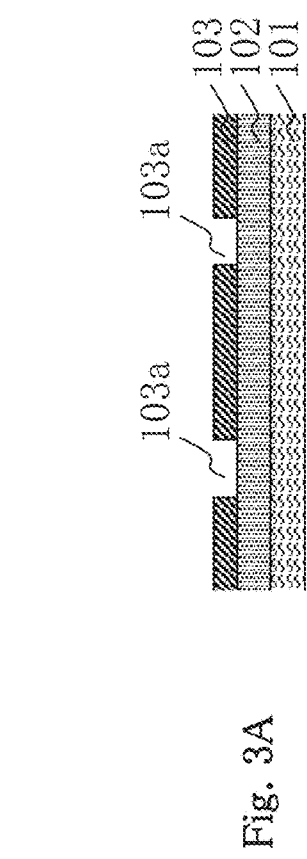

Next, as illustrated in FIG. 3D, the through-hole 119 is formed so as to penetrate from the insulating layer 108 through the non-electrode region 107a and the insulating layer 106, and reach the sacrifice layer 118. The through-hole 119 is a hole for introducing the etchant that removes the sacrifice layer 118. The through-hole 119 may penetrate the sacrifice layer 118 and reach the insulating layer 104 and/or the non-electrode region 103a.

Figure 3E:
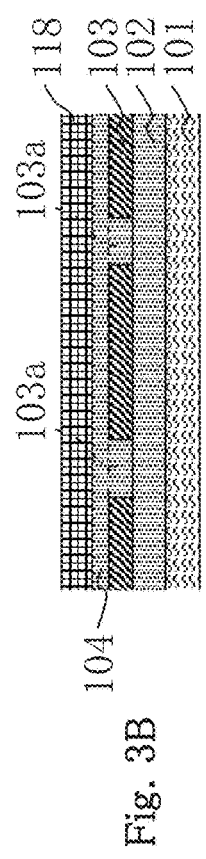

Next, as illustrated in FIG. 3E, the etchant E is introduced via the through-hole 119 and dissolves the sacrifice layer 118, thereby forming the cavity layer 105. For the etchant, an etchant may be used that selectively dissolves the sacrifice layer 118 without dissolving the insulating layers around the cavity layer 105. For example, potassium hydroxide may be used as the etchant E.

Figure 3F:
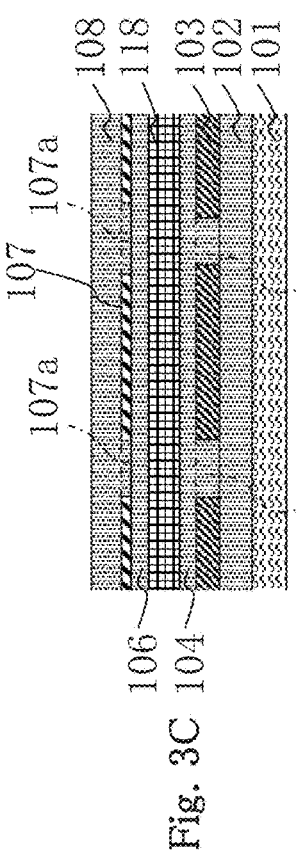

After the etching of the sacrifice layer 118 has sufficiently progressed and the formation of the cavity layer 105 has completed, the through-hole 119 is filled with the insulating material, thereby forming the filled hole 109 as illustrated in FIG. 3F. The ultrasonic transducer is manufactured by the manufacturing method described above.

In the manufacturing method for the ultrasonic transducer described above, the through-hole 119 does not reach the upper electrode 107 or the lower electrode 103 even when the distance between the upper and lower electrodes is reduced to about tens of nm and the through-hole 119 penetrates the sacrifice layer 118. Therefore, there is no risk of the electrodes being dissolved by the etchant. As a result, it is possible to provide an ultrasonic transducer with high yield.

In this manufacturing method, when viewed from above, the through-hole 119 is formed in a region different from the region in which the membrane on top of the cavity layer 105 is formed. As a result, there is no risk of the insulating material that fills the through-hole 119 adhering to the membrane, and a highly reliable ultrasonic transducer can be manufactured.

Additionally, in this manufacturing method, the through-hole 119 is formed from the side where the electrodes and the like are mounted on the substrate 101. As such, the through-hole 119 can be formed without penetrating the substrate 101. Therefore, the through-hole 119 can be formed without performing deep drilling of the substrate, and the ultrasonic transducer can be easily manufactured.

Furthermore, in this manufacturing method, the etchant is introduced after covering the sacrifice layer 118 with the insulating layers that are not etched. As such, only the sacrifice layer 118 is selectively etched and the cavity layer 105 is formed. As a result, in this manufacturing method, the need to control the etching time is eliminated and cavity layers 105 with uniform widths can be formed among the plurality of CMUT elements of the ultrasonic transducer.

Embodiment 2

Hereinafter, the features of an ultrasonic transducer according to Embodiment 2 that differ from the features of the ultrasonic transducer according to Embodiment 1 will be described while referencing FIGS. 4A and 4B. With the ultrasonic transducer according to Embodiment 2, as illustrated in FIG. 4A, the non-electrode region 103a and the region above the non-electrode region 103a are filled with the insulating material to the same height as the insulating layer 104 disposed on the top surface of the lower electrode 103, and are flattened.

As described in the manufacturing method for the ultrasonic transducer according to Embodiment 1, the insulating material is coated on the top surface of the lower electrode 103, the non-electrode region 103a, and above the non-electrode region 103a using a known technique such as plasma CVD or vapor deposition. As a result, an insulating layer 104 with a flat top surface is formed. However, as illustrated in the Comparative Example of FIG. 4B, in actuality, a step shape may form in the sacrifice layer 118. In such cases, and particularly when the thickness of the sacrifice layer 118 is thin, the sacrifice layer 103b of the side wall portion of the step may break and the etchant introduced via the through-hole 119 may not reach the entire sacrifice layer 118, thereby obstructing the formation of the cavity layer 105.

In Embodiment 2, the non-electrode region 103a and the region above the non-electrode region 103a (below the region where the through-hole 119 is provided) are filled with an insulator to the same height as the insulating layer 104 disposed on the top surface of the lower electrode 103, and are flattened. As such, the sacrifice layer 118 is formed on the insulating layer 104 in a flat manner and it is possible to suppress breakage of the sacrifice layer of the side wall portion 103b of the step described above, even when the thickness of the sacrifice layer 118 is thin. As a result, the etchant introduced via the through-hole 119 can reach the entire sacrifice layer 118 and the cavity layer 105 can be formed with good yield.

The insulator filling the non-electrode region 103a and the upper region of the non-electrode region 103a may be formed from the same material as the non-electrode region 103a, the insulating layer 104, or the like, or may be formed from a different material. This insulator may be configured as single layer or as a laminated membrane formed from one or two or more selected from silicon oxide ($SiO_2$), silicon nitride ($Si_3N_4$), aluminum oxide ($Al_2O_3$), titanium oxide ($TiO_2$), zirconium oxide ($ZrO_2$), hafnium oxide ($HfO_2$), silicon-doped hafnium oxide, and the like.

Figure 5A:
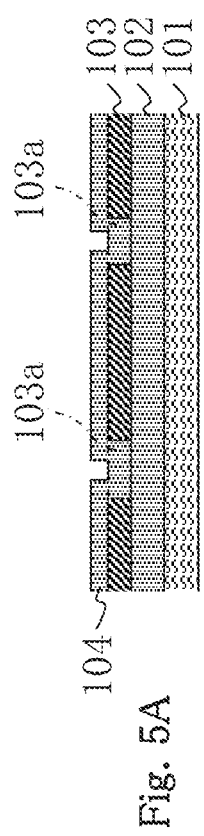
Figure 5B:
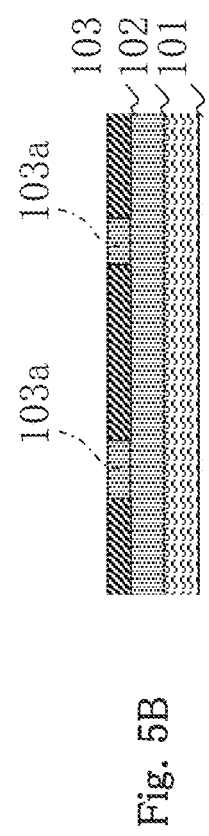
Figure 5C:
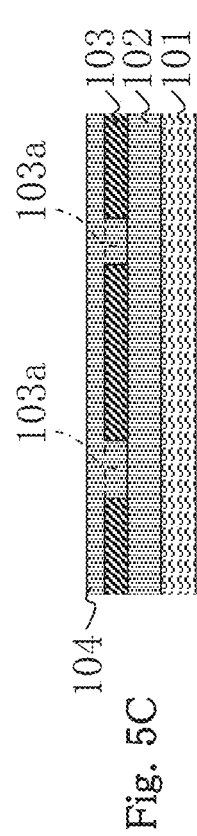

A filling and flattening method for the non-electrode region 103a and the upper region of the non-electrode region 103a is described using FIGS. 5A to 5C. First, as illustrated in FIG. 5A, the insulating layer 102 and the lower electrode 103 are formed on the substrate 101, and the insulating layer 104 is deposited. Next, as illustrated in FIG. 5B, chemical mechanical polishing (CMP) technique or the like is used to remove the insulating layer 104 until the lower electrode 103 is exposed.

Next, as illustrated in FIG. 5C, the insulating layer 104 is formed above the lower electrode 103 and above the non-electrode region 103a.

In the manufacturing method for the ultrasonic transducer according to Embodiment 2, the sacrifice layer 118 can be formed in a flat manner without any steps. As such, the etchant can easily reach the entire sacrifice layer 118 when etching/removing the sacrifice layer 118. As a result, cavity layers 105 with more uniform widths can be formed among the plurality of CMUT elements of the ultrasonic transducer. Therefore, it is possible to manufacture, with increased yield, an ultrasonic transducer with high drive reliability.

Embodiment 3

Hereinafter, an ultrasonic transducer according to Embodiment 3 will be described while referencing FIGS. 6A and 6B. As with the ultrasonic transducer according to Embodiment 2, with the ultrasonic transducer according to Embodiment 3, steps in the sacrifice layer 118 are prevented by modifying the configuration of the portion below the region where the through-hole 119 is provided.

Figure 6A:
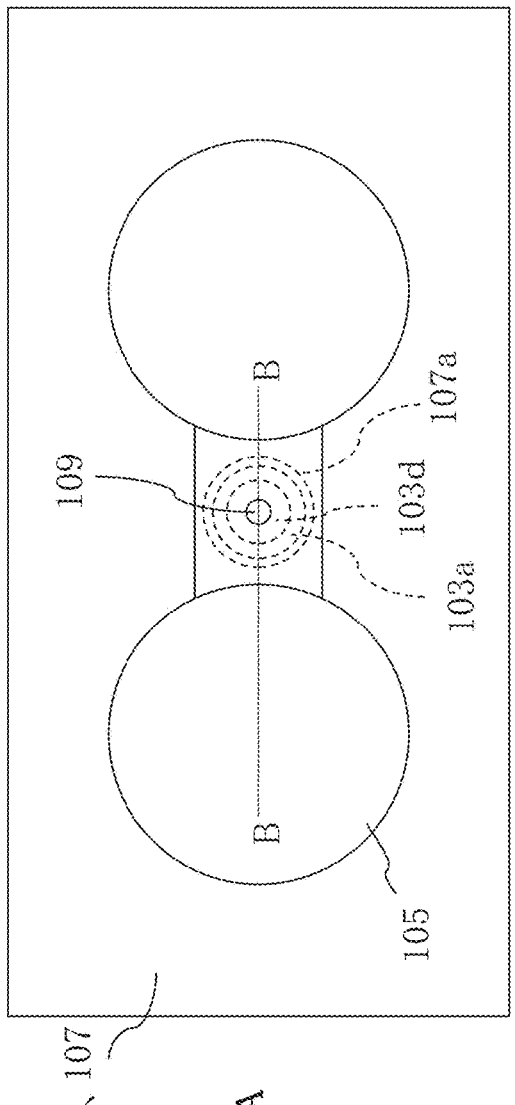
FIG. 6A is a top view of an ultrasonic transducer according to Embodiment 3.
Figure 6B:
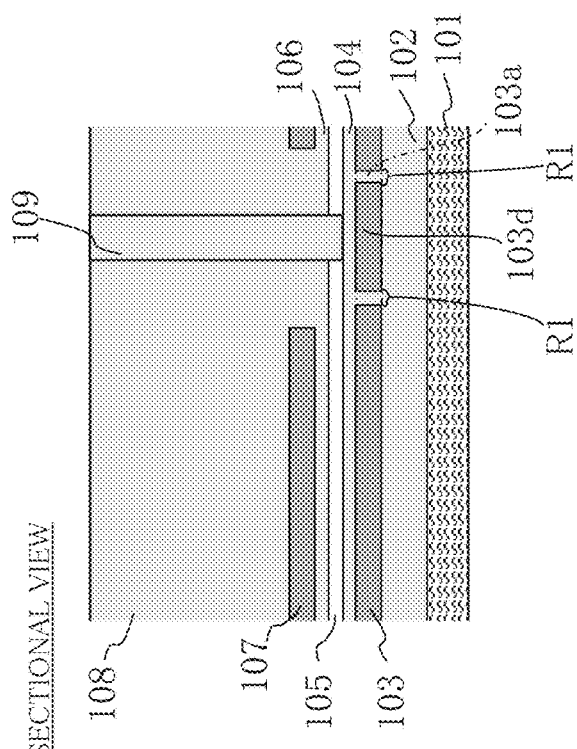
FIG. 6B is a cross-sectional view of the ultrasonic transducer according to Embodiment 3, taken along line B-B of FIG. 6A.

In Embodiment 3, as illustrated in FIGS. 6A and 6B, a non-electrode portion 103d, disposed separated from the lower electrode 103, is provided in the non-electrode region 103a. The non-electrode portion 103d is provided in a region of the portion below the region where the filled hole 109 is formed, and an insulation region R1 is formed on an outer edge of the non-electrode region 103a that contacts the lower electrode 103 (formed between the non-electrode portion 103d and the lower electrode 103).

The non-electrode portion 103d may have a round shape when viewed from above as illustrated in FIG. 6A, or may have a different shape when viewed from above. However, the non-electrode portion 103d preferably has a shape centered in the region directly below the filled hole 109. The size of the non-electrode portion 103d when viewed from above is preferably larger than the size of the filled hole 109. The size of the insulation region R1 when viewed from above is preferably as small as possible.

The non-electrode portion 103d may be formed from the same material as the material of the lower electrode 103, or may be formed from a different material. In one example, the non-electrode portion 103d is formed using Al. Examples of materials other than Al that may be used include metal materials such as Al alloys, W, Ti, TiN, Ni, Co, Cr, Pt, and Au, polycrystalline silicon or amorphous silicon doped with impurities at high concentrations, and indium tin oxide (ITO).

When forming the non-electrode portion 103d from a different material or as a different layer than the lower electrode 103, a different mask than the mask for forming the lower electrode 103 is used and the non-electrode portion 103*d* is formed via a different process than that of the lower electrode 103. However, in cases in which the non-electrode portion 103*d* is formed in the same layer and from the same electrode material as the lower electrode 103, the non-electrode portion 103*d* is formed when forming the lower electrode 103 by using a mask and depositing the electrode material in the regions of the non-electrode region 103*a* other than the insulation region R1. Thus, in cases in which the non-electrode portion 103*d* and the lower electrode 103 are formed from the same material and in the same layer, the number of masks to be used and the number of steps can be reduced compared to when forming from different materials or in different layers. Accordingly, it is preferable that the non-electrode portion 103*d* and the lower electrode 103 be formed from the same material and in the same layer.

With the ultrasonic transducer according to Embodiment 3 described above, the non-electrode portion 103*d* is provided in the region of the portion of the non-electrode region 103*a* below the filled hole 109 and, as such, steps are not formed in the sacrifice layer 118. As a result, it is possible to further enhance the accuracy of the ultrasonic transducer.

In addition, in this manufacturing method for the ultrasonic transducer, even in cases in which the through-hole 119 reaches the non-electrode portion 103*d* and the non-electrode portion 103*d* is removed by the etchant when etching/removing the sacrifice layer 118, the etchant can be prevented from reaching the lower electrode 103 due to the insulation region R1 being formed between the non-electrode portion 103*d* and the lower electrode 103. Furthermore, in this manufacturing method, the need for the filling and flattening process described in Embodiment 2 is eliminated due to the non-electrode portion 103*d* being disposed.

Embodiment 4

Figure 7A:
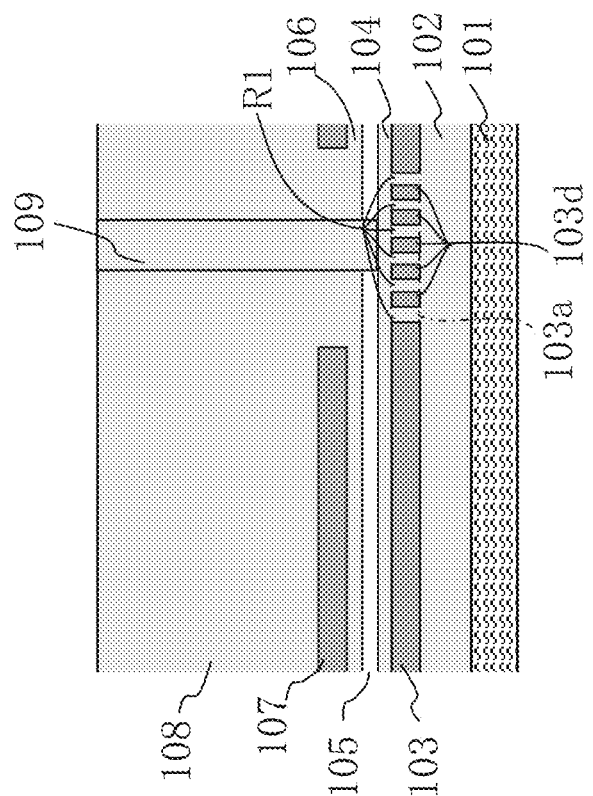
FIG. 7A is a cross-sectional view of an ultrasonic transducer according to Embodiment 4.

In Embodiment 4, as illustrated in FIG. 7A, the non-electrode portion 103*d* described in Embodiment 3 is divided into a plurality of non-electrode portions 103*d*. An insulation region R1 is formed between the outermost non-electrode portion 103*d* and the lower electrode 103, and insulation regions R1 are formed among the plurality of non-electrode portions 103*d* as well.

The non-electrode portion 103*d* may be divided concentrically, in a fan shape, or randomly. The number of divisions of the non-electrode portion 103*d* is not particularly limited.

Even in cases in which the non-electrode portion 103*d* is divided into a plurality of non-electrode portions 103*d* such as in Embodiment 4, the non-electrode portion 103*d* can be manufactured by the same method described for the single non-electrode portion 103*d* of Embodiment 3. It is preferable that all of the divided non-electrode portions 103*d* are formed from the same electrode material and are formed in the same layer.

Figure 7B:
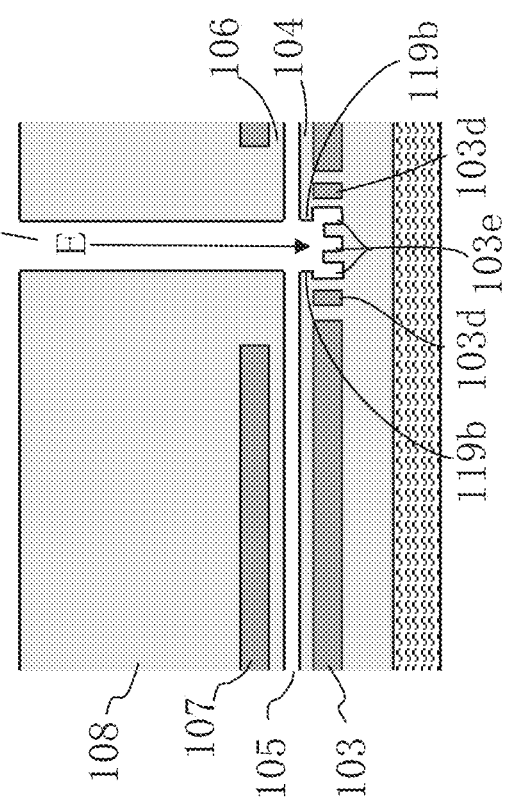
FIG. 7B is a cross-sectional view illustrating a state in which an etchant E is introduced into the ultrasonic transducer according to Embodiment 4.

FIG. 7B illustrates a case in which the through-hole 119 reaches the non-electrode portions 103*d* in the present embodiment. In this case, when the etchant E is introduced through the through-hole 119 in order to form the cavity layer 105, the etchant E only reaches the non-electrode portions 103*d*, of the plurality of non-electrode portions 103*d*, that the through-hole 119 reaches. The non-electrode portions 103*d* that the etchant E reaches are selectively removed and, as a result, cavity portions 103*e* are formed.

In cases in which the non-electrode portions 103*d* are selectively removed and the cavity portions 103*e* are formed, a length by which a region (eave portion) 119*b*, which is around the through-hole 119 and sandwiched between the cavity layer 105 and the cavity portions 103*e*, protrudes toward the through-hole 119 is smaller than that in cases in which all of the non-electrode portions 103*d* are removed. Therefore, in the present embodiment, peeling of the eave portion 119*b* when introducing the etchant can be prevented and an ultrasonic transducer can be manufactured with better yield.

Ultrasonic Imaging Device

Figure 8:
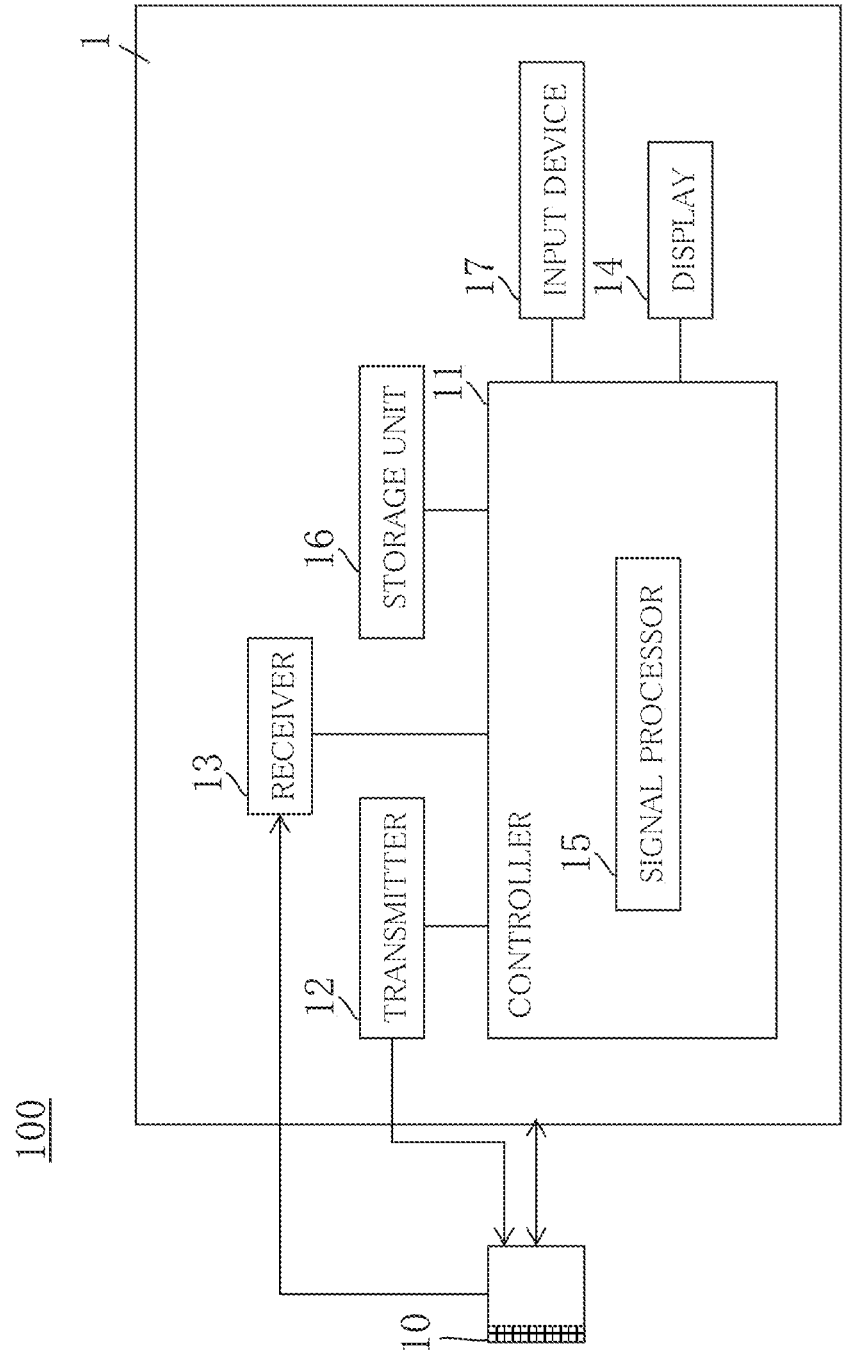
FIG. 8 is a block diagram illustrating a configuration example of an ultrasonic imaging device according to the present invention.

Hereinafter, an ultrasonic imaging device 100 of the present invention will be described using FIG. 8.

The ultrasonic imaging device 100 includes the ultrasonic transducer 10, and a device main body 1 that generates ultrasonic images while controlling the driving of the ultrasonic transducer 10.

The ultrasonic transducer 10 may be provided on an ultrasonic probe that is brought into contact with an inspection subject or is made to contact the inspection subject via a contact medium to transmit and receive ultrasonic waves to and from the inspection subject, or may be provided on a catheter that is inserted into the inspection subject to transmit and receive ultrasonic waves. At least one of the ultrasonic transducers 10 described in Embodiments 1 to 4 above is used in the ultrasonic transducer 10 of the ultrasonic imaging device 100.

The device main body 1 includes a transmitter 12 that transmits electric signals for transmission to the ultrasonic transducer 10; a receiver 13 that receives ultrasonic waves that are the reflected waves from the inspection subject; a controller 11 that controls the operations of the various components; a signal processor 15 that is provided in the controller 11 and that processes the signals received by the receiver 13, creates images, performs various types of calculations, and the like; and a storage unit 16.

The device main body 1 also includes an input device 17 whereby an operator of the ultrasonic imaging device 100 inputs operating conditions of the ultrasonic imaging device 100 into the controller 11, and a display 14 that displays processing results of the signal processor 15 and the like. The input device 17 and the display 14 may function as user interfaces whereby the operator performs interactive operations with the device main body 1.

Configurations of the various components of the device main body 1 are the same as those of known ultrasonic imaging devices. As such, description thereof is omitted.

Next, the operations of the ultrasonic imaging device 100 are briefly described. First, an electric signal for transmission is transmitted, via a digital-analog (D/A) converter (not illustrated in the drawings), from a beamformer of the transmitter 12 to the electrodes 103 and 107 of the ultrasonic transducer 10, and ultrasonic waves are emitted toward the inspection subject from the ultrasonic transducer 10. Acoustic signals reflected during the process of the ultrasonic waves propagating through the inspection subject are received by the ultrasonic transducer 10, converted to digital signals, and transmitted, via an A/D converter (not illustrated in the drawings), as reception data to a receive beamformer of the receiver 13. The receive beamformer carries out addition processing of the signals received by the plurality of elements taking account of the time delay given during transmission. The received signals that have been subjected to the addition processing are then subjected to processing such as attenuation correction by a corrector (not illustrated in the drawings) and, thereafter, are transmitted as RF data to the signal processor 15. The signal processor 15 creates images using the RF data.

The ultrasonic imaging device 100 according to the present invention includes the ultrasonic transducer described in any one of Embodiments 1 to 4. Accordingly, an ultrasonic imaging device capable of high-sensitivity ultrasonic imaging can be provided with good yield. Therefore, this ultrasonic imaging device 100 can be used as an imaging device in, for example, intravascular ultrasound (IVUS) imaging and intravascular photoacoustic (IVPA) imaging, where high-sensitivity imaging is required.

What is claimed is:

1. An ultrasonic transducer including a cavity layer, and a pair of electrodes positioned above and below the cavity layer, the ultrasonic transducer comprising:
   insulating layers disposed above and below each of the pair of electrodes; and
   a filled hole that penetrates, in a vertical direction, at least a portion of the insulating layers positioned above the cavity layer, wherein
   when the ultrasonic transducer is viewed from above, a non-electrode region is provided in each electrode of the pair of electrodes at a position that overlaps the filled hole,
   the non-electrode region positioned on a lower side includes a non-electrode portion formed from a material that is identical to a material of the electrode positioned on the lower side, and
   an insulation region is formed between the non-electrode portion and the electrode positioned on the lower side.

2. The ultrasonic transducer according to claim 1, wherein the filled hole is filled with an insulator.

3. The ultrasonic transducer according to claim 1, wherein the non-electrode region of the electrode, of the pair of electrodes, positioned on a lower side has a size when viewed from above that is smaller than a size of the non-electrode region of the electrode positioned on an upper side.

4. The ultrasonic transducer according to claim 1, wherein a plurality of the non-electrode portions are provided.

* * * * *